(12) United States Patent
VanAtta et al.

(10) Patent No.: US 7,556,373 B2
(45) Date of Patent: Jul. 7, 2009

(54) EYEWEAR WITH RETAINING ASSEMBLY

(75) Inventors: Dylan S. VanAtta, Portland, OR (US); Ryan C. Coulter, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 132 days.

(21) Appl. No.: 11/777,300

(22) Filed: Jul. 13, 2007

(65) Prior Publication Data

US 2009/0015784 A1    Jan. 15, 2009

(51) Int. Cl.
*G02C 5/14* (2006.01)
(52) U.S. Cl. ..................... 351/121; 351/113; 351/116
(58) Field of Classification Search ......... 351/111–123, 351/153, 41; 16/228
See application file for complete search history.

(56) References Cited

U.S. PATENT DOCUMENTS

| | | | |
|---|---|---|---|
| 3,418,041 A | 12/1968 | Courtney | |
| 3,475,084 A | 10/1969 | Gil et al. | |
| 3,762,804 A | 10/1973 | Livas | |
| 4,153,347 A | 5/1979 | Myer | |
| 4,488,792 A | 12/1984 | Wagner | |
| 4,564,272 A | 1/1986 | Rinnooy Kan | |
| 4,986,647 A * | 1/1991 | Blumenthal | 351/51 |
| 5,007,728 A | 4/1991 | Magorien | |
| 5,059,017 A | 10/1991 | Bennato | |
| 5,321,442 A | 6/1994 | Albanese | |
| 5,359,370 A | 10/1994 | Mugnier | |
| 5,386,254 A * | 1/1995 | Kahaney | 351/60 |
| 5,444,876 A | 8/1995 | Cooper et al. | |
| 5,511,251 A | 4/1996 | Brakas | |
| 5,539,561 A | 7/1996 | Khalifa | |
| 5,594,511 A | 1/1997 | Lin | |
| 5,652,637 A | 7/1997 | Marini | |
| 5,668,619 A | 9/1997 | Bolle | |
| 5,781,273 A | 7/1998 | Boden | |
| 5,956,118 A | 9/1999 | Johnson | |
| 5,963,296 A | 10/1999 | Matera | |
| 5,987,702 A | 11/1999 | Simioni | |
| 6,007,199 A | 12/1999 | Yang | |
| 6,099,120 A | 8/2000 | De Lima | |
| 6,231,181 B1 | 5/2001 | Swab | |
| 6,247,811 B1 | 6/2001 | Rhoades et al. | |
| 6,736,504 B1 | 5/2004 | Hermsen | |
| 6,834,952 B2 | 12/2004 | Polovin | |
| 6,865,753 B2 | 3/2005 | Nishida | |
| 6,890,073 B2 | 5/2005 | DiChiara et al. | |
| 6,908,194 B1 | 6/2005 | Johnson | |
| 6,929,365 B2 | 8/2005 | Swab et al. | |
| 6,942,338 B2 | 9/2005 | Ku | |
| 6,969,173 B1 | 11/2005 | Ku | |

(Continued)

FOREIGN PATENT DOCUMENTS

DE      4219039      12/1993

(Continued)

*Primary Examiner*—Huy K Mai
(74) *Attorney, Agent, or Firm*—Banner & Witcoff, Ltd.

(57) ABSTRACT

Eyewear includes a frame and a retaining assembly having right and left connecting members. Each connecting member has a recess with retaining walls extending along opposed sides of the recess. Each of right and left temple connecting members has a substantially T-shaped projection that is configured to be received by a corresponding recess. A retaining member is secured to the right and left temple connecting members.

24 Claims, 4 Drawing Sheets

U.S. PATENT DOCUMENTS

| | | |
|---|---|---|
| 7,033,021 B1 | 4/2006 | Wu |
| 7,059,717 B2 | 6/2006 | Bloch |
| 7,100,215 B2 | 9/2006 | Shiue |
| 7,137,700 B2 | 11/2006 | DiChiara et al. |
| 2006/0007389 A1 | 1/2006 | Fusi et al. |
| 2006/0109419 A1* | 5/2006 | Yves et al. .................. 351/140 |
| 2006/0139567 A1 | 6/2006 | Toulch |

FOREIGN PATENT DOCUMENTS

| | | |
|---|---|---|
| FR | 2700397 | 7/1994 |
| JP | 8094978 | 4/1996 |
| JP | 8166564 | 6/1996 |
| JP | 11223799 | 8/1999 |

* cited by examiner

EYEWEAR WITH RETAINING ASSEMBLY

FIELD OF THE INVENTION

This invention relates generally to eyewear, and, in particular, to eyewear with a retaining assembly that provides for a removable retainer, such as temple arms or a strap.

BACKGROUND OF THE INVENTION

Eyewear is well known for use in many activities including athletic activities, such as biking, skiing, and running. The eyewear may have a multitude of constructions. For example, the eyewear may have a wraparound lens secured to a frame, commonly referred to as a shield lens, or it may have two distinct lenses secured to a frame. The eyewear has a retaining member for securing the eyewear to the user's head. In certain constructions, the eyewear has a pair of temple arms that rest on top of the user's ears to secure the eyewear to the user's head. The eyewear may also be provided with a stretchable strap connected at opposed ends thereof to the eyewear frame, with the strap encircling the user's head to secure the eyewear to the user's head. Eyewear with straps is often used by athletes to prevent the eyewear from being jostled or shaken from the user's head.

It would be desirable to provide eyewear with a retaining assembly that allows a user to exchange one retaining member, such as a pair of temple arms, for another, such as a strap. Particular objects and advantages will be apparent to those skilled in the art, that is, those who are knowledgeable or experienced in this field of technology, in view of the following disclosure of the invention and detailed description of certain embodiments.

SUMMARY

The principles of the invention may be used to advantage to provide eyewear with a retaining assembly allowing a retaining member to be removably secured to the eyewear frame. In accordance with a first aspect, eyewear includes a frame having a right side and a left side. A retaining assembly includes a right connecting member on the right side of the frame having a first recess. The first recess includes a first retaining wall extending along a portion of a first side of the first recess and a second retaining wall extending along a second side of the first recess. A left connecting member on the left side of the frame includes a second recess. The second recess includes a first retaining wall extending along a portion of a first side of the second recess and a second retaining wall extending along a second side of the second recess. A right temple connecting member has a first substantially T-shaped projection on a front portion thereof, with the first projection configured to be received by the first recess. A left temple connecting member has a second substantially T-shaped projection on a front portion thereof, with the second projection configured to be received by the second recess. A retaining member is secured to the right temple connecting member and the left temple connecting member.

In accordance with another aspect, eyewear includes a frame having a right side and a left side and at least one lens secured to the frame. A retaining assembly includes a right connecting member on the right side of the frame having a first recess. The first recess includes a first retaining wall extending along a portion of a first side of the first recess, a second retaining wall extending along a second side of the first recess, a first sloped surface extending from a front surface of the first retaining wall to a lower surface of the first retaining wall, and a second sloped surface extending from a front surface of the second retaining wall to a lower surface of the second retaining wall. A left connecting member on the left side of the frame includes a second recess. The second recess includes a first retaining wall extending along a portion of a first side of the second recess and a second retaining wall extending along a second side of the second recess, a first sloped surface extending from a front surface of the first retaining wall to a lower surface of the first retaining wall, and a second sloped surface extending from a front surface of the second retaining wall to a lower surface of the second retaining wall. A right temple connecting member has a first substantially T-shaped projection on a front portion thereof, with the first projection is configured to be received by the first recess. The first substantially T-shaped projection includes a first trunk portion and a first cross portion, with a lower portion of a rear surface of the first cross portion sloping downwardly and rearwardly. A left temple connecting member has a second substantially T-shaped projection on a front portion thereof, with the second projection configured to be received by the second recess. The second substantially T-shaped projection includes a second trunk portion and a second cross portion, with a lower portion of a rear surface of the second cross portion sloping downwardly and rearwardly. A retaining member is secured to the right temple connecting member and the left temple connecting member.

In accordance with a further aspect, eyewear includes a frame having a right side and a left side. A first lens and a second lens are secured to the frame. A retaining assembly includes a right connecting member on the right side of the frame having a first recess. The first recess includes a first retaining wall extending along a portion of a first side of the first recess, a second retaining wall extending along a second side of the first recess, a first sloped surface extending from a front surface of the first retaining wall to a lower surface of the first retaining wall, and a second sloped surface extending from a front surface of the second retaining wall to a lower surface of the second retaining wall. A left connecting member on the left side of the frame includes a second recess. The second recess includes a first retaining wall extending along a portion of a first side of the second recess and a second retaining wall extending along a second side of the second recess, a first sloped surface extending from a front surface of the first retaining wall to a lower surface of the first retaining wall, and a second sloped surface extending from a front surface of the second retaining wall to a lower surface of the second retaining wall. A right temple connecting member has a first substantially T-shaped projection on a front portion thereof, with the first projection configured to be received by the first recess. The first substantially T-shaped projection includes a first trunk portion and a first cross portion, with a lower portion of a rear surface of the first cross portion sloping downwardly and rearwardly. A left temple connecting member has a second substantially T-shaped projection on a front portion thereof, with the second projection configured to be received by the second recess. The second substantially T-shaped projection includes a second trunk portion and a second cross portion, with a lower portion of a rear surface of the second cross portion sloping downwardly and rearwardly. A retaining member is secured to the right temple connecting member and the left temple connecting member. A first biasing member is positioned on the front portion of the right temple connecting member; and a second biasing member is positioned on the front portion of the left temple connecting member.

Substantial advantage is achieved by providing eyewear with a retaining assembly. In particular, certain embodiments allow a user to easily remove a retaining member, such as a pair of temple arms, and replace it with another retaining member, such as a strap or another pair of temple arms, for example.

These and additional features and advantages disclosed here will be further understood from the following detailed disclosure of certain embodiments.

The figures referred to above are not drawn necessarily to scale, should be understood to provide a representation of particular embodiments of the invention, and are merely conceptual in nature and illustrative of the principles involved. Some features of the eyewear with a retaining assembly depicted in the drawings have been enlarged or distorted relative to others to facilitate explanation and understanding. The same reference numbers are used in the drawings for similar or identical components and features shown in various alternative embodiments. Eyewear with a retaining assembly as disclosed herein would have configurations and components determined, in part, by the intended application and environment in which they are used.

DETAILED DESCRIPTION OF CERTAIN PREFERRED EMBODIMENTS

Figure 1:
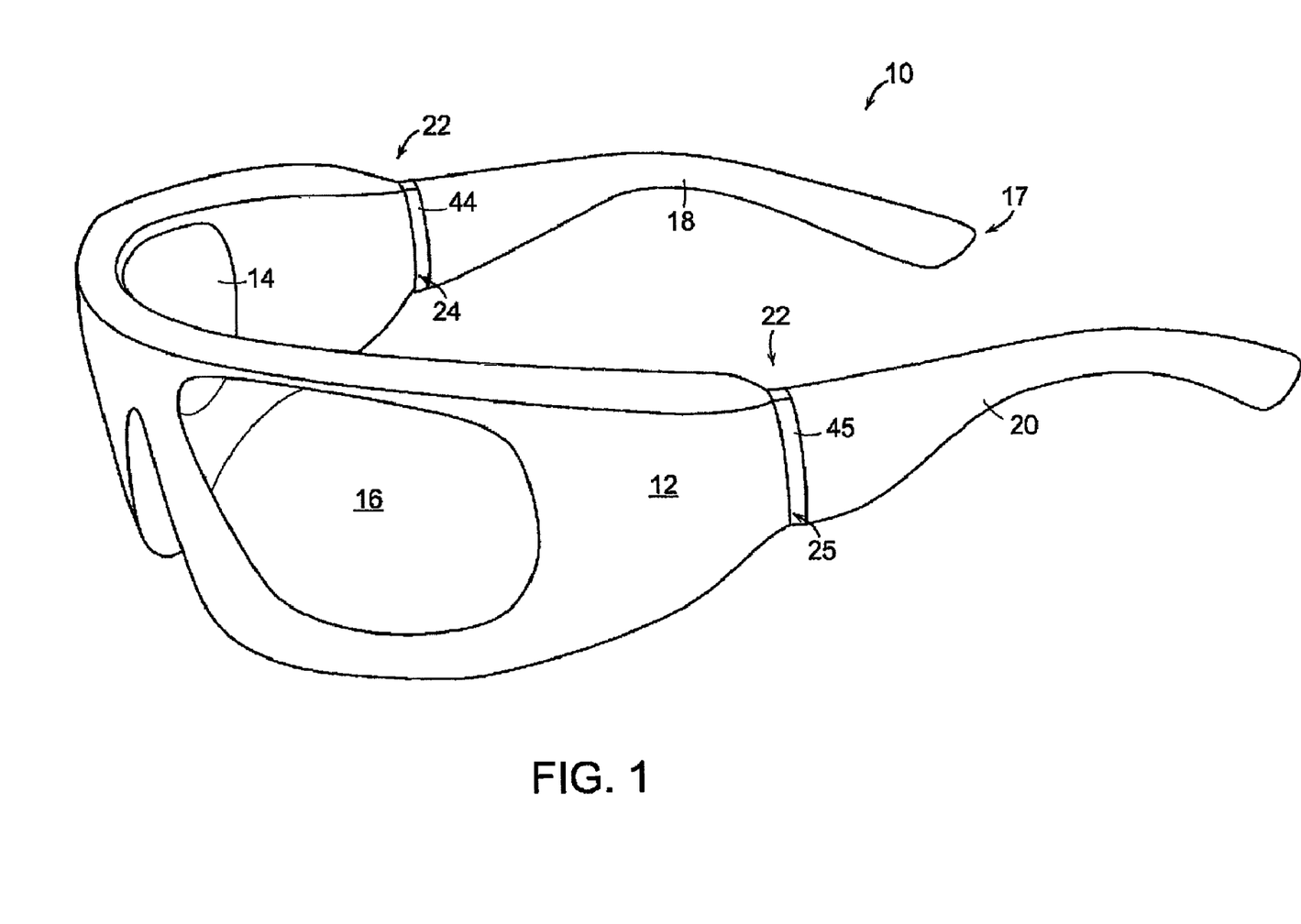
FIG. 1 is a perspective view of eyewear with a retaining assembly, shown with a pair of temple arms.

The present invention may be embodied in various forms. A preferred embodiment of eyewear 10 is shown in FIG. 1. Certain directional terms used herein refer to directions with respect to the wearer of eyewear 10. Thus, the terms outward, outwardly, forward, and forwardly, as used herein, refer to a surface facing away from, or a direction extending away from, or an element spaced from, the face of a wearer of eyewear 10. The terms inward, inwardly, rear, and rearwardly refer to a surface facing toward, or a direction extending toward, the face of a wearer of eyewear 10. The terms left and right are considered to be used with respect to the wearer of eyewear 10. Thus, for example, left of, or to the left, refers to a direction toward the wearer's left.

Eyewear 10 includes a frame 12, a first or right lens 14 secured within frame 12, and a second or left lens 16 secured within frame 12. Right lens 14 and left lens 16 may be removably secured within frame 12 such that they can be replaced. This is especially advantageous for users that need to adapt to different lighting condition, and may be useful to accommodate prescription lenses, for example.

Frame 12 may be formed of a rigid material, for example, a fiber-reinforced material such as a carbon fiber composite, providing a rigid structure and support for right and left lenses 14, 16. In other embodiments, frame 12 may be formed of plastic, or a rubber-coated core material, such as metal or plastic. Other suitable materials for frame 12 will become readily apparent to those skilled in the art, given the benefit of this disclosure.

Although the embodiment illustrated in FIG. 1 shows eyewear 10 with two separate lenses, it is to be appreciated that the present invention may be incorporated in eyewear having a single lens or shield lens, embodiments of which are often referred to as performance eyewear. Such performance eyewear is often used by athletes, e.g., bicycle riders and runners. It is to be appreciated that eyewear 10 is meant to include not only performance eyewear, but rather, all types of eyewear, including, for example, safety glasses.

Frame 12 is secured to a user's head through the use of a retaining member 17. In the embodiment illustrated in FIG. 1, retaining member 17 includes a pair of temple arms 18, 20. Thus, a first or right temple arm 18 is secured to frame 12 and a second or left temple arm 20 is secured to frame 12. In the illustrated embodiment, right temple arm 18 and left temple arm 20 are rigidly secured to outer frame 12. It is to be appreciated that in other embodiments, right temple arm 18 and left temple arm 20 may be pivotally secured to outer frame 12.

Temple arms 18, 20 may be formed of any suitable material, including, for example, plastic, or a rubber coated core material, such as metal or plastic. In certain preferred embodiments, temple arms 18, 20 are formed of a flexible, resilient material, such as beta titanium. In other embodiments, temple arms 18, 20 may be formed of a rigid material, such as a fiber-reinforced material, e.g., a carbon fiber composite. Other suitable materials for temple arms 18, 20 will become readily apparent to those skilled in the art, given the benefit of this disclosure.

A retaining assembly 22 is used to removably secure retaining member 17 to frame 12 and is seen in FIGS. 2-7. In the illustrated embodiment, retaining assembly 22 includes a right connecting member 24 for removably securing right temple arm 18 to frame 12, and a left connecting member 25 for removably securing left temple arm 20 to frame 12. Right connecting member 24 and left connecting member 25 may be separate elements secured to frame 12 with suitable fastening means, such as screws or adhesive, for example, or they may be, as illustrated here, of unitary, that is, one-piece construction with frame 12. Similarly, right connecting member 24 and left connecting member 25 may of unitary construction with right temple arm 18 and left temple arm 20, respectively.

Figures 2, 3, 4, 5:
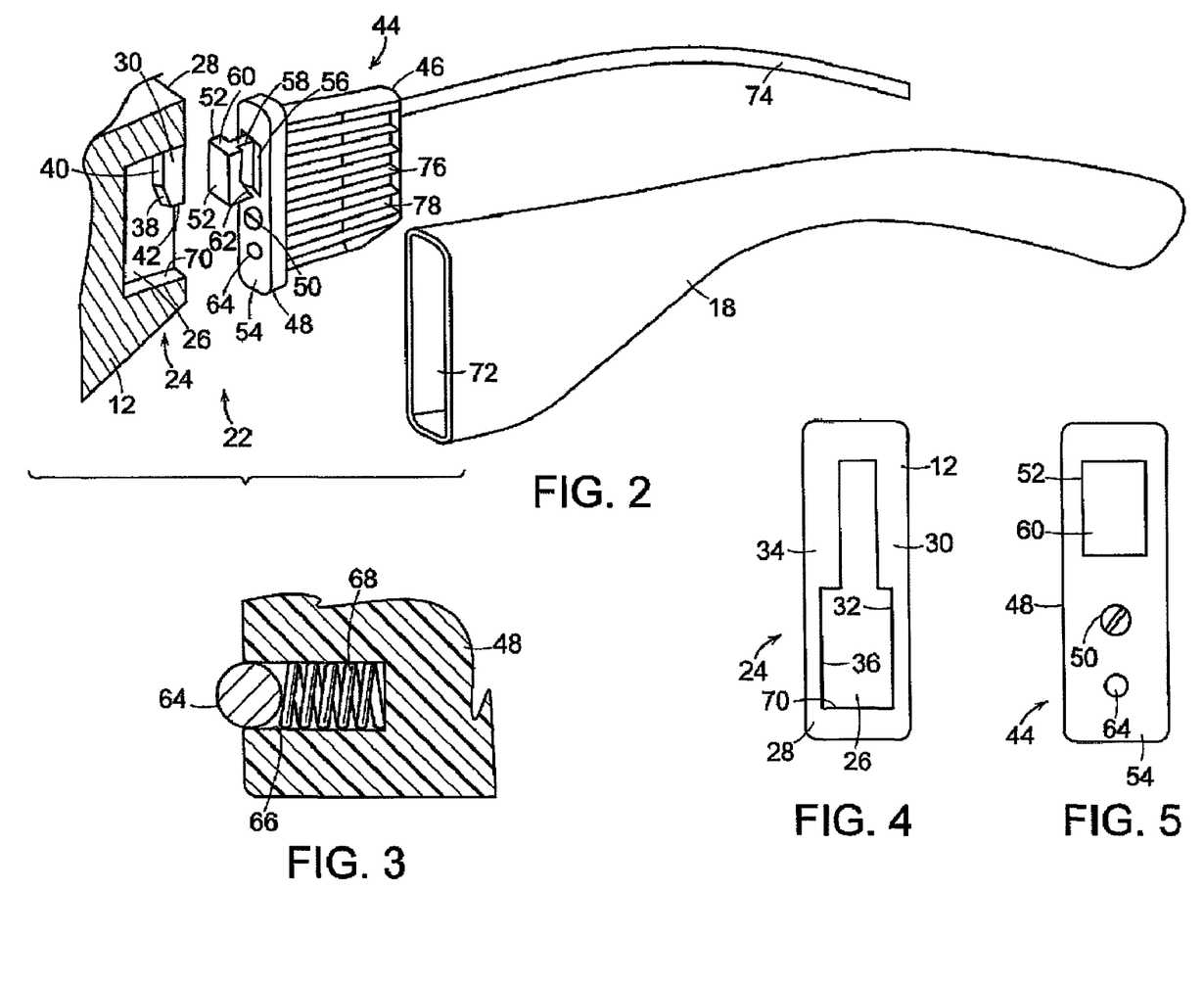
FIG. 2 is an exploded view, partially in section, of the retaining assembly of the eyewear of FIG. 1.
FIG. 3 is a section view of a temple connecting member of the retaining assembly of FIG. 2.
FIG. 4 is an elevation view of the connecting member of the retaining assembly of FIG. 2.
FIG. 5 is an elevation view of the temple connecting member of the retaining assembly of FIG. 2.

A first recess 26 is formed in a rear portion, such as rear surface 28, of right connecting member 24. A first retaining wall 30 extends along an upper portion of a first sidewall 32 of first recess 26. A second retaining wall 34 extends along an upper portion of a second sidewall 36 of first recess 26 opposite first sidewall 32. In certain embodiments, a sloped surface 38 is formed along a lower portion of the front of first retaining wall 30 and second retaining wall 34, sloping downwardly and rearwardly from a front surface 40 of each retaining wall 30, 34 to a bottom or lower surface 42 of each retaining wall.

Left connecting member 25, which is not shown in detail here, has a construction identical to that of right connecting member 24, including a second recess with corresponding first and second retaining walls and sloped surfaces formed thereon.

Retaining assembly 22 includes a right temple connecting member 44 and a left temple connecting member 45. Only right temple connecting member 44 will be described in detail here. Right temple connecting member 44 includes a base portion 46 and a plate 48 secured to a front surface of base portion 46 with a fastener such as a screw 50. In other embodiments, plate 48 may be secured to base portion 46 with adhesive or any other suitable fastener. Other suitable fasteners will become readily apparent to those skilled in the art, given the benefit of this disclosure. In the illustrated embodiment, base portion 46 is formed of a plastic material such as a nylon, for example Nylon 12, which is often referred to as TR-90 Nylon, Nylon 6, or a fiber-filled nylon. Plate 48 is formed of a metal such as stainless steel, aluminum, or any other suitable metal. Other suitable materials for base portion 46 and plate 48 will become readily apparent to those skilled in the art, given the benefit of this disclosure.

A substantially T-shaped projection 52 extends outwardly from a front surface 54 of plate 48. In the illustrated embodiment, projection 52 is of unitary construction with base portion 46 and extends outwardly through an aperture 56 formed in plate 48. It is to be appreciated that projection 52 could be a separate element secured to right temple connecting member 44.

Substantially T-shaped projection 52 includes a trunk portion 58 extending from plate 48 and a cross portion 60 positioned at the end of trunk portion 58. A lower portion of the rear surface of cross portion 60 extends downwardly and rearwardly to form a sloped surface 62. Sloped surface 62 engages sloped surface 38 of retaining walls 30, 34 as described in greater detail below.

A first biasing member 64 is provided on a lower portion of front surface 54 of plate 48. In the illustrated embodiment, the biasing member is a first ball 64, shown in FIG. 3, seated in a first cylinder 66 formed in plate 48, with a first spring 68 biasing first ball 64 outwardly. First ball 64 engages a lower surface 70 of first recess 26, which acts as a detent, when retaining assembly 22 is in its assembled condition, as described in greater detail below.

Base portion 46 of right temple connecting member 44 is received within a recess 72 formed in temple arm 18. In certain embodiments, a core wire 74 extends rearwardly from base portion 46 of right temple connecting member 44. Temple arm 18 may, in certain embodiments, be formed of a material that is injected about core wire 74, such as a rubber-coated plastic, for example.

In certain embodiments, base portion 46 may include a plurality of substantially horizontally extending ridges 76 and corresponding grooves 78 formed therein. Ridges 76 and grooves 78 provide for improved aesthetics in eyewear in which temple arms 18, 20 are formed of a transparent or translucent material.

It is to be appreciated that left temple connecting member 45, not shown in detail here, has a construction identical to that of right temple connecting member 44, and engages left connecting member 25 in similar fashion to removably secure left temple arm 20 to frame 12. Left temple connecting member 45 would, therefore, include a second substantially T-shaped projection with a corresponding sloped surface and a second biasing member such as a second spring-loaded ball.

Figure 6:
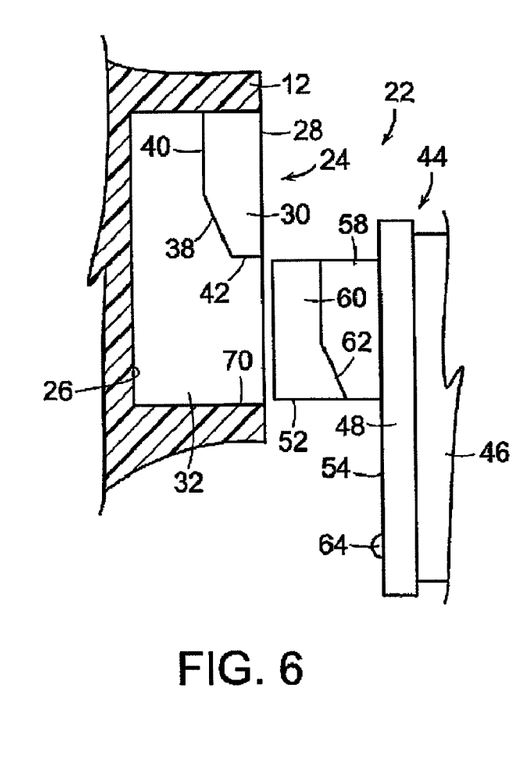
FIG. 6 is a section view of the retaining assembly of FIG. 2, shown just prior to engagement of the temple connecting member with the connecting member.
Figure 7:
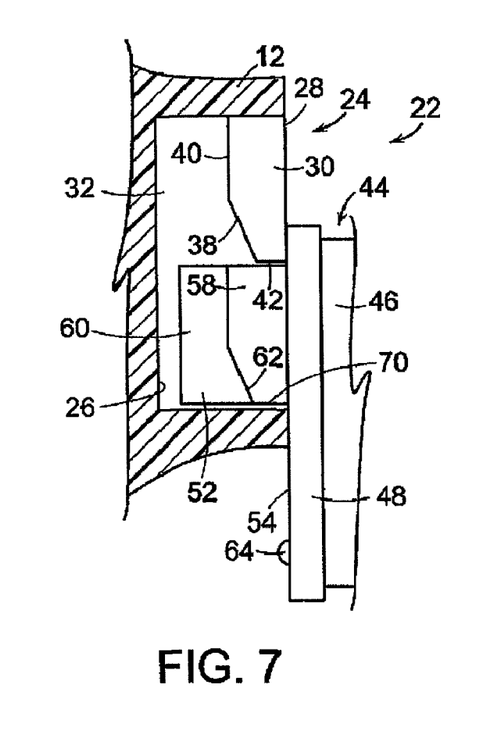
FIG. 7 is a section view of the retaining assembly of FIG. 2, shown with the temple connecting member partially engaged with the connecting member.
Figure 8:
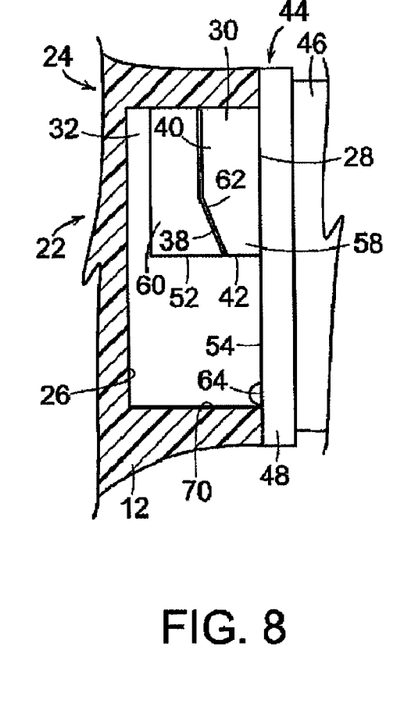
FIG. 8 is a section view of the retaining assembly of FIG. 2, shown with the temple connecting member fully engaged with the connecting member.

The assembly of retaining assembly 22 through the engagement of right temple connecting member 44 with right connecting member 24 is illustrated in FIGS. 6-8. Initially, substantially T-shaped projection 52 of right temple connecting member 44 is inserted into first recess 26 below first and second retaining walls 30, 34 (second retaining wall 34 is not visible in these section views). Projection 52 is inserted until front surface 54 of plate 48 engages the rear surface of connecting member 24 and cross portion 60 is just past front surface 40 of first retaining wall 30 and the corresponding front surface of second retaining wall 34, as seen in FIG. 7. Right temple connecting member 44 is then raised, with cross portion 60 of projection 52 sliding upwardly along front surface 40 of first retaining wall 30 and the corresponding front surface of second retaining wall 34. Projection 52 is slid upwardly until sloped surface 62 of projection 52 engages sloped surface 38 of first retaining wall 30 and the corresponding sloped surface of second retaining wall 34. As projection 52 reaches this position, ball 64, which was depressed into cylinder 66 as it came into contact with the wall of connecting member 44, springs forwardly with its lower surface engaging lower surface 70 of first recess 26 in ball-detent fashion.

In this position, right temple connecting member 44 is retained in an engaged position with connecting member 24 by virtue of the fact that cross portion 60 of projection 52 is captured by first and second retaining walls 30, 34, preventing right temple connecting member 44 from moving rearwardly away from connecting member 24; and by the engagement of ball 64 with lower surface 70 of recess 26 in ball-detent fashion, which keeps right temple connecting member 44 from moving downwardly with respect to connecting member 24.

To separate right temple connecting member 44 and connecting member 24, the user grasps right temple connecting member 44 and pushes it downwardly, forcing ball 64 into cylinder 66, thereby allowing free downward movement of right temple connecting member 44. Right temple connecting member 44 is moved downwardly until cross portion 60 of projection 52 is free of first and second retaining walls 30, 34, at which point it is pulled toward the rear and away from connecting member 24.

The same procedure described above with respect to right connecting member 24 and right temple connecting member 44 is used to engage left connecting member 25 and corresponding left temple connecting member 45 of retaining assembly 22.

Figure 9:
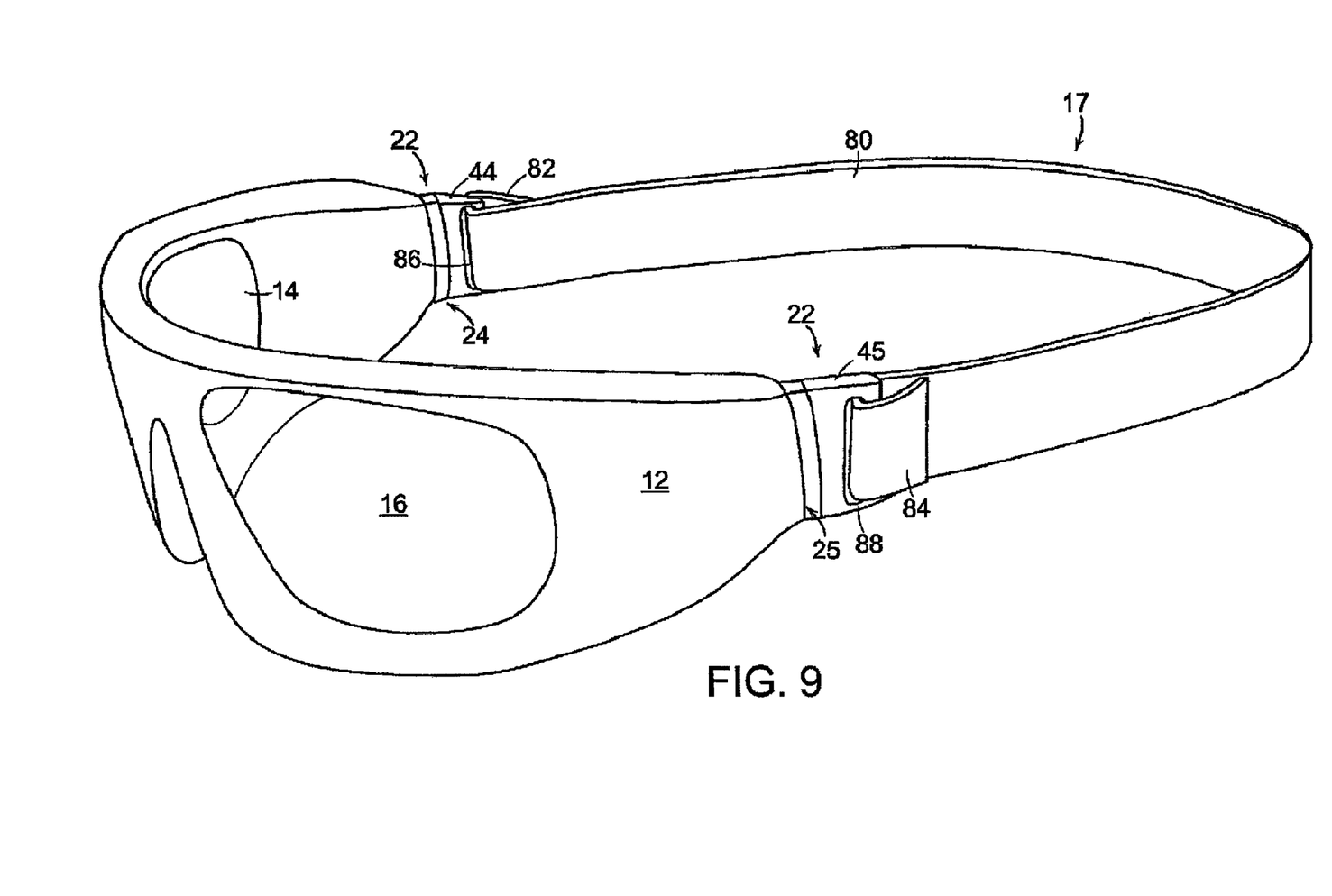
FIG. 9 is a perspective view of eyewear with a retaining assembly, shown with a retaining strap.

In another embodiment, illustrated in FIG. 9, retaining member 17 is formed of a strap 80, having a first end 82 secured to right temple connecting member 44, and a second end 84 connected to left temple connecting member 45. In the illustrated embodiment, right temple connecting member 44 includes a first loop 86, with first end 82 of strap 80 extending through loop 86 and being secured to strap 80 by stitching or other suitable fastening means. Similarly, left temple connecting member 45 includes a second loop 88, with second end 84 of strap 80 extending through loop 88 and being secured to strap 80 by stitching or other suitable fastening means. In certain embodiments, strap 80 is formed of a stretchable, resilient material such as an elastic band having a rubber elastic material sewn into a woven strap, silicone, or neoprene, for example, which allows strap 80 to be comfortably stretched about a user's head, yet providing enough tension to keep eyewear 10 on the user's head even during vigorous athletic activities.

By providing retaining assembly 22 with right and left connecting members 24, 25 and right and left temple connecting members 44, 45, a user can easily remove one retaining member 17 from eyewear 10 and replace it with another retaining member 17. Thus a user can switch from using temple arms to using a strap, or vice versa. Additionally, a user can switch from one particular temple arm, or temple arms, to a different type of temple arm or temple arms. Such flexibility will allow a user to replace a broken temple arm, or to switch to a temple arm or arms of a different style or color, or a temple arm having any other desired characteristic, aesthetic or otherwise.

Thus, while there have been shown, described, and pointed out fundamental novel features of various embodiments, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is the intention, therefore, to be limited only as indicated by the scope of the claims appended hereto.

What is claimed:

1. Eyewear comprising, in combination:
   a frame having a right side and a left side; and
   a retaining assembly comprising:
      a right connecting member on the right side of the frame and including a first recess, the first recess including a first retaining wall extending along a portion of a first side of the first recess and a second retaining wall extending along a second side of the first recess;
      a left connecting member on the left side of the frame and including a second recess, the second recess including a first retaining wall extending along a portion of a first side of the second recess and a second retaining wall extending along a second side of the second recess;
      a right temple connecting member having a first substantially T-shaped projection on a front portion thereof, the first projection configured to be received by the first recess;
      a left temple connecting member having a second substantially T-shaped projection on a front portion thereof, the second projection configured to be received by the second recess; and
      a first biasing member on the front portion of the right temple connecting member; and
      a second biasing member on the front portion of the left temple connecting member.

2. The eyewear of claim 1, wherein the frame includes a lens.

3. The eyewear of claim 1, wherein the frame includes a pair of lenses.

4. The eyewear of claim 1, further comprising a retaining member connected to the right temple connecting member and the left temple connecting member.

5. The eyewear of claim 4, wherein the retaining member comprises:
   a right temple arm connected to the right temple connecting member; and
   a left temple arm connected to the left temple connecting member.

6. The eyewear of claim 4, wherein the retaining member comprises a strap connected to the right temple connecting member and the left temple connecting member.

7. The eyewear of claim 6, wherein the right temple connecting member includes a first loop, a first end of the strap being connected to the first loop, and a second loop, a second end of the strap being connected to the second loop.

8. The eyewear of claim 1, further comprising:
   a first core wire extending rearwardly from the right temple connecting member; and
   a second core wire extending rearwardly from the left temple connecting member.

9. The eyewear of claim 8, further comprising:
   a right temple arm receiving the first core wire; and
   a left temple arm receiving the second core wire.

10. The eyewear of claim 1, wherein the first biasing member comprises a first cylinder formed in the right temple connecting member, a first ball seated in the first cylinder, and a first spring biasing the first ball forwardly; and
   the second biasing member comprises a second cylinder formed in the left temple connecting member, a second ball seated in the second cylinder, and a second spring biasing the second ball forwardly.

11. The eyewear of claim 10, wherein the first ball is positioned within the first recess slightly above a lower edge of the first recess when the right temple connecting member is engaged with the right connecting member; and
   the second ball is positioned within the second recess slightly above a lower edge of the second recess when the left temple connecting member is engaged with the left connecting member.

12. The eyewear of claim 10, wherein the first ball is positioned within the first recess and is in contact with a lower edge of the first recess when the right temple connecting member is engaged with the right connecting member; and
   the second ball is positioned within the second recess and is in contact with a lower edge of the second recess when the left temple connecting member is engaged with the left connecting member.

13. The eyewear of claim 1, wherein the right temple connecting member comprises a base portion and a plate secured to a front surface of the base portion, the first substantially T-shaped projection extending outwardly from a front surface of the plate; and
   the left temple connecting member comprises a base portion and a plate secured to a front surface of the base portion, the second substantially T-shaped projection extending outwardly from a front surface of the plate.

14. The eyewear of claim 1, wherein each of the first and second retaining walls includes a sloped surface extending from a front surface thereof to a lower surface thereof.

15. The eyewear of claim 1, wherein each of the first and second substantially T-shaped projections includes a trunk portion and a cross portion and a sloped surface extending from a rear surface of the cross portion to a lower surface of the cross portion.

16. Eyewear comprising, in combination:
   a frame having a right side and a left side;
   at least one lens secured to the frame; and
   a retaining assembly comprising:
      a right connecting member on the right side of the frame and including a first recess, the first recess including a first retaining wall extending along a portion of a first side of the first recess, a second retaining wall extending along a second side of the first recess, a first sloped surface extending from a front surface of the first retaining wall to a lower surface of the first retaining wall, and a second sloped surface extending from a front surface of the second retaining wall to a lower surface of the second retaining wall;
      a left connecting member on the left side of the frame and including a second recess, the second recess including a first retaining wall extending along a portion of a first side of the second recess and a second retaining wall extending along a second side of the second recess, a first sloped surface extending from a front surface of the first retaining wall to a lower surface of the first retaining wall, and a second sloped surface extending from a front surface of the second retaining wall to a lower surface of the second retaining wall;

a right temple connecting member having a first substantially T-shaped projection on a front portion thereof, the first projection configured to be received by the first recess, the first substantially T-shaped projection including a first trunk portion and a first cross portion, a lower portion of a rear surface of the first cross portion sloping downwardly and rearwardly;

a left temple connecting member having a second substantially T-shaped projection on a front portion thereof, the second projection configured to be received by the second recess, the second substantially T-shaped projection including a second trunk portion and a second cross portion, a lower portion of a rear surface of the second cross portion sloping downwardly and rearwardly; and a first biasing member on the front portion of the right temple connecting member; and a second biasing member on the front portion of the left temple connecting member.

17. The eyewear of claim 16, further comprising a retaining member connected to the right temple connecting member and the left temple connecting member.

18. The eyewear of claim 17, wherein the retaining member comprises:
   a right temple arm connected to the right temple connecting member; and
   a left temple arm connected to the left temple connecting member.

19. The eyewear of claim 17, wherein the retaining member comprises a strap connected to the right temple connecting member and the left temple connecting member.

20. The eyewear of claim 16, wherein the first biasing member comprises a first cylinder formed in the right temple connecting member, a first ball seated in the first cylinder, and a first spring biasing the first ball forwardly; and
   the second biasing member comprises a second cylinder formed in the left temple connecting member, a second ball seated in the second cylinder, and a second spring biasing the second ball forwardly.

21. Eyewear comprising, in combination:
   a frame having a right side and a left side;
   a first lens secured to the frame;
   a second lens secured to the frame;
   a retaining assembly comprising:
      a right connecting member on the right side of the frame and including a first recess, the first recess including a first retaining wall extending along a portion of a first side of the first recess, a second retaining wall extending along a second side of the first recess, a first sloped surface extending from a front surface of the first retaining wall to a lower surface of the first retaining wall, and a second sloped surface extending from a front surface of the second retaining wall to a lower surface of the second retaining wall;

a left connecting member on the left side of the frame and including a second recess, the second recess including a first retaining wall extending along a portion of a first side of the second recess and a second retaining wall extending along a second side of the second recess, a first sloped surface extending from a front surface of the first retaining wall to a lower surface of the first retaining wall, and a second sloped surface extending from a front surface of the second retaining wall to a lower surface of the second retaining wall;

a right temple connecting member having a first substantially T-shaped projection on a front portion thereof, the first projection configured to be received by the first recess, the first substantially T-shaped projection including a first trunk portion and a first cross portion, a lower portion of a rear surface of the first cross portion sloping downwardly and rearwardly; and a left temple connecting member having a second substantially T-shaped projection on a front portion thereof, the second projection configured to be received by the second recess, the second substantially T-shaped projection including a second trunk portion and a second cross portion, a lower portion of a rear surface of the second cross portion sloping downwardly and rearwardly;

a retaining member connected to the right temple connecting member and the left temple connecting member; and a first biasing member on the front portion of the right temple connecting member; and a second biasing member on the front portion of the left temple connecting member.

22. The eyewear of claim 21, wherein the retaining member comprises:
   a right temple arm connected to the right temple connecting member; and
   a left temple arm connected to the left temple connecting member.

23. The eyewear of claim 21, wherein the retaining member comprising a strap connected to the right temple connecting member and the left temple connecting member.

24. The eyewear of claim 21, wherein the first biasing member comprises a first cylinder formed in the right temple connecting member, a first ball seated in the first cylinder, and a first spring biasing the first ball forwardly; and
   the second biasing member comprises a second cylinder formed in the left temple connecting member, a second ball seated in the second cylinder, and a second spring biasing the second ball forwardly.

* * * * *